US008816686B2

(12) United States Patent
Park et al.

(10) Patent No.: US 8,816,686 B2
(45) Date of Patent: Aug. 26, 2014

(54) PET-MRI CONVERGENCE SYSTEM

(75) Inventors: HyunWook Park, Daejeon (KR);
MyungSung Song, Daejeon (KR)

(73) Assignee: Korea Advanced Institute of Science and Technology (KR)

( * ) Notice: Subject to any disclaimer, the term of this patent is extended or adjusted under 35 U.S.C. 154(b) by 242 days.

(21) Appl. No.: 13/224,866

(22) Filed: Sep. 2, 2011

(65) Prior Publication Data

US 2012/0223715 A1    Sep. 6, 2012

(30) Foreign Application Priority Data

Sep. 2, 2010  (KR) .................. 10-2010-0085884

(51) Int. Cl.
*G01V 3/00* (2006.01)
(52) U.S. Cl.
USPC .......................................... 324/318; 600/411
(58) Field of Classification Search
USPC ........... 324/318, 322, 307, 309, 300; 600/411
See application file for complete search history.

(56) References Cited

U.S. PATENT DOCUMENTS

| 7,667,457 | B2* | 2/2010 | Linz et al. | 324/307 |
| 7,728,590 | B2* | 6/2010 | Eberler et al. | 324/318 |
| 7,937,131 | B2* | 5/2011 | Cho et al. | 600/415 |
| 8,131,340 | B2* | 3/2012 | Eberlein et al. | 600/411 |
| 2013/0241555 | A1* | 9/2013 | Obata et al. | 324/318 |

FOREIGN PATENT DOCUMENTS

KR    1020090068416    6/2009

* cited by examiner

*Primary Examiner* — Louis Arana
(74) *Attorney, Agent, or Firm* — The Belles Group, P.C.

(57) ABSTRACT

A positron emission tomography (PET)-magnetic resonance imaging (MRI) convergence system. In one aspect, the invention may be a PET-MRI convergence system including: a cylindrical magnet bore which includes an outer wall and an inner wall; a gradient magnet which is disposed adjacent to the inner wall of the magnet bore; a MRI RF coil which is disposed adjacent to the inner wall of the gradient magnet, emits an RF pulse signal and detects MRI data corresponding to the RF pulse signal; and a PET detector which is spaced apart from the MRI RF coil and is disposed adjacent to the inner wall of the gradient magnet, and detects PET data.

7 Claims, 2 Drawing Sheets und detecting PET data from the examinee, wherein the MRI region and PET region are arranged on the same line on the inner wall of the gradient magnet.

PET-MRI CONVERGENCE SYSTEM

CROSS-REFERENCE TO RELATED APPLICATIONS

This application claims priority under 35 U.S.C. §119 to Korean Patent Application No. 10-2010-0085884, filed on Sep. 2, 2010, the entirety of which is hereby incorporated herein by reference.

FIELD OF THE INVENTION

The present invention relates to a convergence system, and more particularly to a positron emission tomography (PET)-magnetic resonance imaging (MRI) convergence system.

BACKGROUND OF THE INVENTION

In general, a positron emission tomography (hereafter, referred to as PET) device is used to form an image of a particular human organ or a tumor or used to form an image for diagnosing biochemical phenomena of metabolic activity areas. The PET device generates a tomographic image by marking a radioactive isotope which emits positrons on various basic metabolites and injecting it to a human body, and by detecting, outside the body, gamma ray generated from the interaction between the positron and the metabolites.

A PET image obtained by the PET device generally has low resolution. For this reason, in the past, the low resolution of the PET image has been compensated by using the PET device together with a computer tomography (hereafter, referred to as CT) device. However, a CT image obtained by the CT device generally has a low contrast to soft-tissues.

Therefore, in the past, a positron emission tomography-magnetic resonance imaging (PET-MRI) convergence system has been developed which has a high contrast to soft-tissues of a human body, provides molecular images and functional images and uses the PET device together with a magnetic resonance imaging (MRI) device without radiation exposure.

FIG. 1 is a view showing a cross section of a prior PET-MRI convergence system. Referring to FIG. 1, in the prior PET-MRI convergence system 100, a PET detector 130 and an MRI RF coil 120 are in parallel arranged to have the same field of view (FOV). In other words, the PET detector 130 is located between the MRI RF coil 120 and a magnet bore 101.

The PET-MRI convergence system 100 causes an interaction between PET and MRI. Many noises are hereby generated, which degrades image quality. The noise is caused by MRI, for example, a high magnetic field, high frequency high power interference and low frequency high power interference and the like. The noise is also caused by PET, for example, magnetism distortion, signal-to-noise ratio reduction and Eddy current and the like. Here, particularly, since the high magnetic field caused by MRI and radio frequency energy caused by MRI have much influence on the PET, an RF shielding 140 is placed between the MRI RF coil 120 and the PET detector 130 in order to minimize the influence. However, when the RF shielding 140 is placed, the RF shielding 140 deteriorates the performance of the MRI RF coil 120 and the performance of an RF receiver 150, generates Eddy current in a gradient magnet 110, so that the resolution of an MRI image is degraded.

The RF receiver 150 is fixed and installed on a carrier 160 carrying an examinee 170. In obtaining the MRI image, the installation location of the RF receiver 150 is not considered. However, in obtaining a PET image, the RF receiver 150 may have much influence on the PET image.

Since the PET detector 130 is disposed farther from the circular centric point of the magnet bore 101 than the MRI RF coil 120, a gamma ray emitted from the examinee 170 is attenuated and scattered by the MRI RF coil 120, so that the intensity of the gamma ray is reduced.

Additionally, as shown in FIG. 1, the prior PET-MRI convergence system 100 in which the PET detector 130 and the MRI RF coil 120 are disposed in parallel with each other has a problem in that the size of the outermost magnet bore 101 should be increased in order to obtain the field of views (FOV) of the MRI and PET.

In order to reduce the influence of the PET device on the MRI image, a non-magnetic material may be used in the PET detector 130, an optical amplifier and an electronic circuit and the like of the PET-MRI convergence system 100. However, it is difficult to use the non-magnetic material in all the elements. For example, the non-magnetic material cannot be used in the capacitor and the resistance element of a pre-amplifier disposed inside the magnet bore 101. Therefore, the magnetic component present inside the PET detector 130 affects the main magnetic field uniformity of MRI. Further, the PET detector 130, the RF shielding 140 and other electronic circuits may generate the Eddy current by interacting with the signals generated from the gradient magnet 110. The Eddy current reduces the signal-to-noise ratio of the MRI image and the quality of an image obtained through the PET-MRI convergence system 100 is deteriorated.

SUMMARY OF THE INVENTION

One aspect of the present invention is a PET-MRI convergence system. The PET-MRI convergence system includes: a cylindrical magnet bore which includes an outer wall and an inner wall; a gradient magnet which is disposed adjacent to the inner wall of the magnet bore; a MRI RF coil which is disposed adjacent to the inner wall of the gradient magnet, emits an RF pulse signal and detects MRI data corresponding to the RF pulse signal; and a PET detector which is spaced apart from the MRI RF coil and is disposed adjacent to the inner wall of the gradient magnet, and detects PET data.

It is desirable that the PET detector should be disposed on both sides of the MRI RF coil respectively.

It is desirable that the PET-MRI convergence system further should include an RF shielding which is disposed adjacent to the PET detector and blocks the RF pulse signal emitted from the MRI RF coil.

It is desirable that the PET-MRI convergence system further should include a data processor which receives the MRI data from the MRI RF coil, receives the PET data from the PET detector and generates a PET-MRI converged image.

It is desirable that the PET-MRI convergence system further should include a carrier which passes through the middle of the magnet bore and carries an examinee.

Another aspect of the present invention is a PET-MRI convergence system. The PET-MRI convergence system includes: a carrier carrying an examinee along its movement axis; a magnet bore surrounding the movement axis of the carrier and generating a static magnetic field; a gradient magnet being disposed on the inner wall of the magnet bore and generating a gradient magnetic field; an MRI region being disposed on the inner wall of the gradient magnet in such a manner as to surround the movement axis of the carrier and detecting MRI data from the examinee; and a PET region being disposed on the inner wall of the gradient magnet in such a manner as to surround the movement axis of the carrier and detecting PET data from the examinee. A plurality of the PET regions is provided and the MRI region is located between the plurality of the PET regions.

It is desirable that the MRI region should emit an RF pulse signal to the examinee and should obtain the MRI data corresponding to the RF pulse signal from the examinee.

It is desirable that the PET-MRI convergence system further should include a data processor which receives the MRI data and the PET data and generates a PET-MRI converged image.

DETAILED DESCRIPTION

The aforementioned objectives, characteristics and advantages will become apparent with the following detailed description accompanied with related drawings. It can be understood that the technical idea of the present invention will be easily embodied by those skilled in the art. In the following description of the present invention, the detailed description of known functions and configurations incorporated herein is omitted when it may make the subject matter of the present invention rather unclear. Hereafter, an exemplary embodiment of the present invention will be described in detail with reference to the accompanying drawings.

Figure 1:
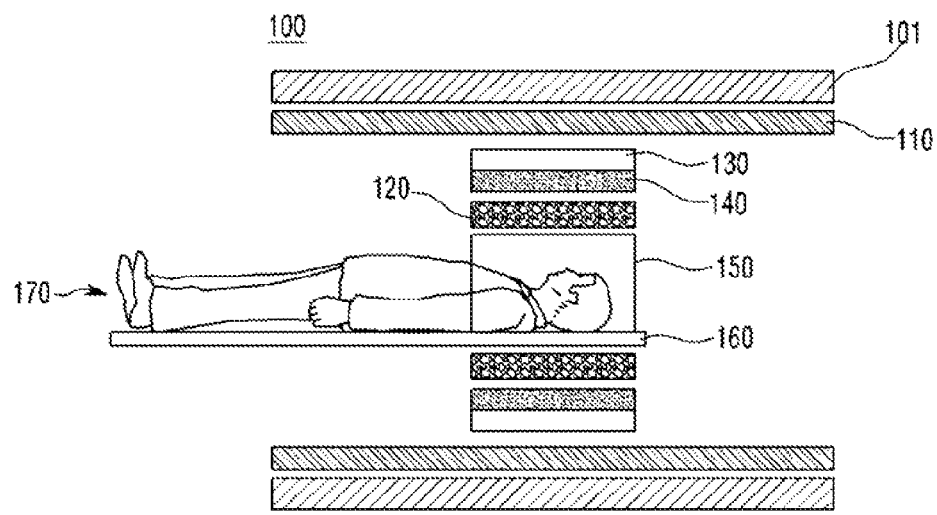
FIG. 1 is a cross sectional view of a prior PET-MRI convergence system.
Figure 2:
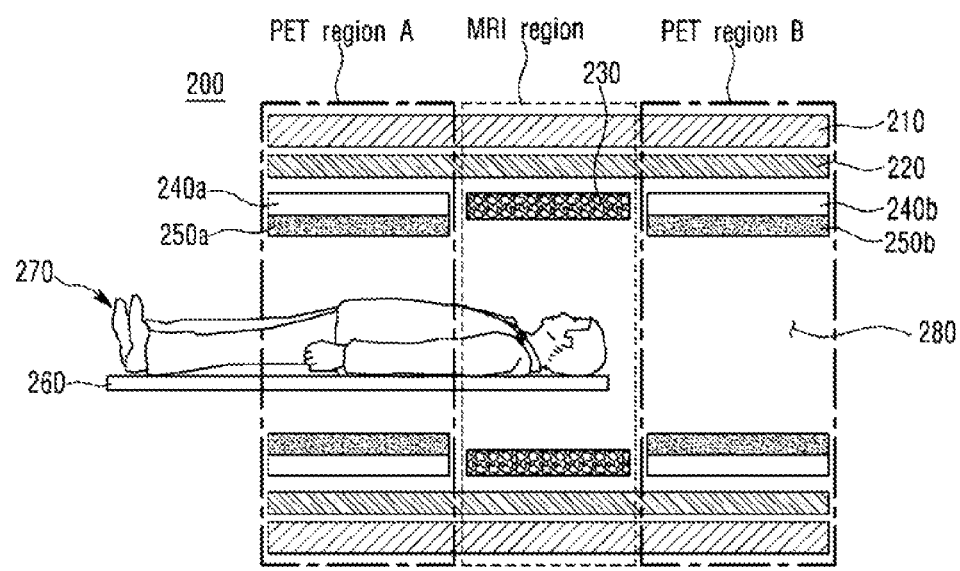
FIG. 2 is a cross sectional view of a PET-MRI convergence system according to an exemplary embodiment of the present invention.

FIG. 2 is a cross sectional view of a PET-MRI convergence system 200 according to an exemplary embodiment of the present invention. Though not shown in FIG. 2, it should be understood that while the external appearance of the PET-MRI convergence system 200 according to the embodiment of the present invention is similar to those of a typical PET system, a typical MRI system and a typical PET-MRI convergence system, the internal structure of the PET-MRI convergence system 200 is different from those of the aforementioned typical systems. This will be described in detail below.

Referring to FIG. 2, the PET-MRI convergence system 200 according to an exemplary embodiment of the present invention includes an MRI region and a PET region. The MRI region is for obtaining magnetic resonance data of an examinee 270. The PET region is for obtaining positron emission tomography data of the examinee 270. The PET-MRI convergence system 200 also includes a through-hole 280 for allowing a carrier 260 carrying the examinee 270 to easily come in and out. The diameter of the through-hole 280 depends on the thicknesses of a magnet bore 210, a gradient magnet 220 and an MRI RF coil 230 or the thicknesses of magnet bore 210, the gradient magnet 220 and PET detectors 240a and 240b.

The MRI region and the PET region are disposed in series in the direction of the movement axis of the carrier 260 carrying the examinee 270. Here, it is recommended that the PET region should be disposed on both sides of the MRI region. Here, it is noted that one PET region may be disposed apart from the MRI region.

The MRI region includes the magnet bore 210, the gradient magnet 220 and the MRI RF coil 230. The PET region includes the magnet bore 210, the gradient magnet 220, the PET detectors 240a and 240b and RF shielding 250a and 250b. Hereafter, the components will be described in detail.

The magnet bore 210 is a main magnet and surrounds the movement axis of the carrier 260. Here, it is recommended that the magnet bore 210 should have a cylindrical structure comprised of an outer wall and an inner wall. When the magnet bore 210 operates, a static magnetic field which is parallel with the movement axis of the carrier 260 is generated within the through-hole 280 by the magnet bore 210.

The gradient magnet 220 is disposed adjacent to the inner wall of the magnet bore 210. When the gradient magnet 220 operates, the gradient magnet 220 generates a gradient magnetic field which forms a predetermined angle with the static magnetic field generated from the magnet bore 210.

The MRI RF coil 230 is disposed adjacent to the inner wall of the gradient magnet 220. When the static magnetic field and the gradient magnetic field are generated from the magnet bore 210 and the gradient magnet 220 respectively, the MRI RF coil 230 has a signal transmission function of emitting an RF pulse signal corresponding to Lamor frequency. The MRI RF coil 230 also has a receiving function of receiving MRI data emitted from the examinee 270.

Here, the detailed operation of the MRI RF coil 230 will be described. When the MRI RF coil 230 emits an RF pulse signal, the emitted pulse signal is added to the examinee 270 on the carrier 260. Then, the examinee 270 emits the MRI data corresponding to Lamor frequency of the added RF pulse signal. At this moment, the MRI RF coil 230 collects the MRI data emitted from the examinee 270.

The PET detectors 240a and 240b are disposed adjacent to the inner wall of the gradient magnet 220 and disposed apart from the MRI RF coil 230. That is, the PET detectors 240a and 240b and the MRI RF coil 230 are adjacent to the inner wall of the gradient magnet 220 and disposed on the same plane, and the PET detectors 240a and 240b are not directly connected to and disposed apart from the MRI RF coil 230 at a predetermined interval.

When the examinee 270 enters a PET region A (or a PET region B), the PET detectors 240a and 240b detect PET data (gamma ray) emitted from the examinee 270.

Here, the PET detectors 240a and 240b may further include the RF shielding 250a and 250b.

The RF shielding 250a and 250b are disposed adjacent to the inner walls of the PET detectors 240a and 240b and block the RF pulse signal emitted from the MRI RF coil 230 within the MRI region.

The carrier 260 carries the examinee 270 along the movement axis, i.e., the central axis of the through-hole 280. Since the carrier 260 does not include a receiver receiving the MRI data or the PET data, the carrier 260 has a simple structure and prevents the examinee 270 of a patient from feeling inconvenient and anxious due to an enclosed space.

Meanwhile, though not shown in FIG. 2, the PET-MRI convergence system 200 may further include a data processor (not shown).

The data processor (not shown) collects the MRI data obtained from the MRI RF coil 230 of the MRI region and the PET data obtained from the PET detectors 240a and 240b of the PET regions A and B, and generates a PET-MRI converged image.

Figure 3:
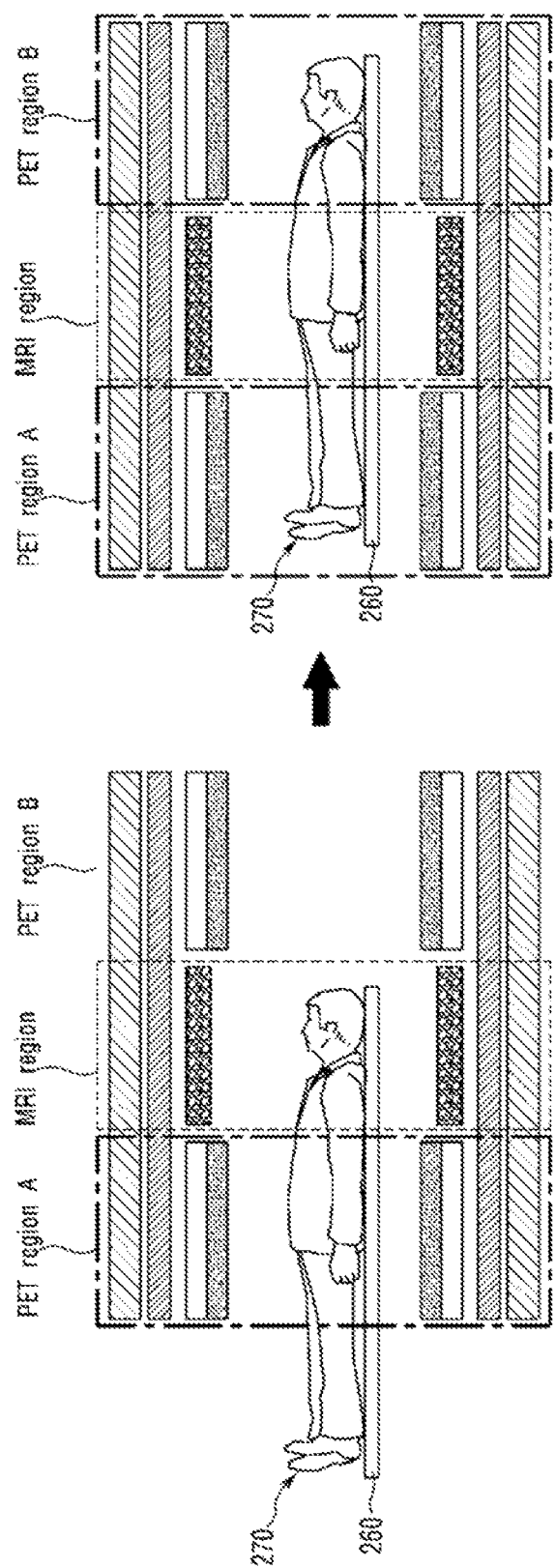
FIG. 3 is a view for describing an operation of the PET-MRI convergence system shown in FIG. 2 according to the exemplary embodiment of the present invention.

FIG. 3 is a view for describing an operation of the PET-MRI convergence system 200 shown in FIG. 2 according to the exemplary embodiment of the present invention.

Referring to FIG. 3, for the purpose of detecting the PET data, the carrier 260 is moved in such a manner that a body part to be measured of the examinee 270 (for example, abdomen) is located in the middle of the PET region A, and the PET data is detected. Here, when the abdomen of the examinee 270 is located in the PET region A, the head of the examinee 270 may be located in the MRI region, so that the PET data of the abdomen and the MRI data of the head can be detected at the same time.

Subsequently, after the carrier 260 carries the abdomen of the examinee 270 to the MRI region, the MRI data of the abdomen is detected. Here, the PET data of the head of the examinee 270 and the PET data of the lower part of the body of the examinee 270 can be detected at the same time.

As described above, the PET-MRI convergence system 200 according to the exemplary embodiment of the present invention is able to detect the MRI data and the PET data of the examinee 270 at the same time or drive the operations of the PET and MRI at a predetermined time interval.

The PET-MRI convergence system 200 according to the exemplary embodiments of the present invention shown in FIGS. 2 and 3 is able to simultaneously detect the MRI data and the PET data either of a predetermined body part or the whole body of the examinee 270. Particularly, since the MRI RF coil 230 within the MRI region is fixed and installed in the middle of the magnet bore 210, the MRI data for the whole body of the examinee 270 can be easily obtained.

When the PET data of the examinee 270 is detected, a structure for detecting the MRI data is not present around the examinee 270. Therefore, pure PET data of the examinee 270 can be obtained due to no artifacts.

Furthermore, because the PET regions A and B are disposed on both sides of the MRI region, respectively, a time required for taking a full length photography of the examinee 270 can be reduced.

Further, in the past, since the MRI device and the PET device are installed within the magnet bore in parallel with each other, the PET-MRI convergence system should inevitably have a large volume. However, in the PET-MRI convergence system according to the exemplary embodiment of the present invention, the MRI device and the PET device are disposed in series, so that the volume of the PET-MRI convergence system can be reduced.

When it is assumed that the prior PET-MRI convergence system and the PET-MRI convergence system based on the exemplary embodiment of the present invention have the same volume, the PET-MRI convergence system based on the exemplary embodiment of the present invention includes the through-hole 280 larger than that of the prior PET-MRI convergence system and has higher space efficiency.

Additionally. MRI data distortion caused by the PET, artifacts and a reduction of signal-to-noise ratio can be decreased and negative influence of the PET data by the MRI can be reduced. Accordingly, the sensitivity of the PET data can be improved.

The PET-MRI convergence system 200 of the present invention makes it possible to take a full length photography of a human body. The PET-MRI convergence system 200 has an excellent determination capability of soft-tissues within a human body, provides molecular images and functional images, and has no radiation exposure The PET-MRI convergence system 200 obtains MRI data and PET data of a human body at the same time by one measurement. The PET-MRI convergence system 200 separately photographs MRI and PET and overcomes the problems caused by the interaction between the MRI and the PET.

The PET-MRI convergence system 200 is able to minimize the interaction between the MRI and the PET and maximize a space for photographing.

As described above, since it will be understood by those skilled in the art that various changes in form and details may be made therein without departing from the spirit and scope of the invention as defined by the appended claims, the present invention is not limited to the embodiment described above and the accompanying drawings.

What is claimed is:

1. A PET-MRI convergence system comprising:
a cylindrical magnet bore having an outer wall and an inner wall;
a gradient magnet disposed adjacent to the inner wall of the magnet bore;
an MRI RF coil disposed adjacent to a first portion of the inner wall of the gradient magnet, the MRI RF coil emitting an RF pulse signal and detecting MRI data corresponding to the RF pulse signal; and
a PET detector spaced apart from the MRI RF coil and disposed adjacent to a second portion of the inner wall of the gradient magnet, the second portion being different from the first portion, the PET detector detecting PET data, wherein the PET detector is disposed on both sides of the MRI RF coil respectively.

2. The PET-MRI convergence system of claim 1, further comprising an RF shielding disposed adjacent to the PET detector and blocking the RF pulse signal emitted from the MRI RF coil.

3. The PET-MRI convergence system of claim 2, further comprising a data processor which receives the MRI data from the MRI RF coil, receives the PET data from the PET detector and generates a PET-MRI converged image.

4. The PET-MRI convergence system of claim 2, further comprising a carrier which passes through the middle of the magnet bore and carries an examinee.

5. A PET-MRI convergence system comprising:
a carrier carrying an examinee along its movement axis;
a magnet bore surrounding the movement axis of the carrier and generating a static magnetic field;
a gradient magnet disposed on the inner wall of the magnet bore and generating a gradient magnetic field;
an MRI region disposed on a first portion of the inner wall of the gradient magnet in such a manner as to surround the movement axis of the carrier, the MRI region detecting MRI data from the examinee; and
a PET region disposed on a second portion of the inner wall of the gradient magnet in such a manner as to surround the movement axis of the carrier, the second portion being, different from the first portion, the PET region detecting PET data from the examinee,
wherein a plurality of the PET regions are provided and the MRI region is located between the plurality of the PET regions.

6. The PET-MRI convergence system of claim 5, wherein the MRI region emits an RF pulse signal to the examinee and obtains the MRI data corresponding to the RF pulse signal from the examinee.

7. The PET-MRI convergence system of claim 6, further comprising a data processor which receives the MRI data and the PET data and generates a PET-MRI converged image.

* * * * *